US009498188B2

(12) United States Patent
Ma et al.

(10) Patent No.: US 9,498,188 B2
(45) Date of Patent: Nov. 22, 2016

(54) ENHANCED ULTRASOUND IMAGING APPARATUS AND ASSOCIATED METHODS OF WORK FLOW

(75) Inventors: Qinglin Ma, Woodinville, WA (US); Nikolaos Pagoulatos, Bothell, WA (US); Dave Glenn Willis, Woodinville, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 195 days.

(21) Appl. No.: 13/555,008

(22) Filed: Jul. 20, 2012

(65) Prior Publication Data

US 2014/0024938 A1 Jan. 23, 2014

(51) Int. Cl.
*A61B 8/00* (2006.01)
*A61B 8/08* (2006.01)
(52) U.S. Cl.
CPC ............... *A61B 8/523* (2013.01); *A61B 8/483* (2013.01); *A61B 8/463* (2013.01)
(58) Field of Classification Search
USPC .......................... 600/440; 382/128; 345/419
See application file for complete search history.

(56) References Cited

U.S. PATENT DOCUMENTS

| 6,775,404 | B1 | 8/2004 | Pagoulatos et al. |
| 7,130,457 | B2 * | 10/2006 | Kaufman et al. ............. 382/128 |
| 2005/0187474 | A1 * | 8/2005 | Kwon ........................... 600/437 |
| 2009/0054776 | A1 * | 2/2009 | Sasaki ........................... 600/443 |
| 2011/0255762 | A1 * | 10/2011 | Deischinger et al. ........ 382/131 |

* cited by examiner

*Primary Examiner* — Long V Le
*Assistant Examiner* — Ellsworth Weatherby
(74) *Attorney, Agent, or Firm* — Perkins Coie LLP

(57) ABSTRACT

Enhanced ultrasound imaging apparatus and associated methods of work flow are disclosed herein. In one embodiment, a method of ultrasound scanning includes receiving a first dataset representing ultrasonic scanning of a target anatomy of a patient in a two-dimensional mode and generating a two-dimensional ultrasound image of the scanned target anatomy based on the received first dataset. The method also includes receiving an input defining at least one of an A-plane, a B-plane, and a C-plane on the displayed two-dimensional ultrasound image. Thereafter, a second dataset representing ultrasonic scanning of the target anatomy in a three-dimensional mode is received and an additional ultrasound image along a plane orthogonal to the two-dimensional ultrasound image of the target anatomy is generated based on (1) the three-dimensional scanning and (2) the input defining at least one of the A-plane, the B-plane, and the C-plane.

10 Claims, 8 Drawing Sheets

ENHANCED ULTRASOUND IMAGING APPARATUS AND ASSOCIATED METHODS OF WORK FLOW

TECHNICAL FIELD

The present application is generally related to a 3-D/4-D ultrasound imaging apparatus and associated methods of work flow.

BACKGROUND

Ultrasound volume imaging is capable of recording and/or displaying three- or four-dimensional (3D space plus time) visual information of a human anatomy. Such techniques have been used for visualizing and/or diagnosing conditions relating to obstetrics, gynecology, and cardiology. For example, ultrasound volume imaging can be used in gynecology to visualize and/or diagnose various uterus abnormalities. FIG. 1A shows a cross-sectional view of normal female reproductive organs. In contrast, FIG. 1B shows a cross-sectional view of female reproductive organs with various abnormalities including fibroids 102 (e.g., submuscosal, intramural, and subserosal), a polyp 104, adenomyosis 106, an ovarian cyst 108, and a partial septum 110. In another example, ultrasound volume imaging can also be used to assess uterine shapes for infertility diagnosis. It is believed that uteri may have some variations that correlate to high risks of miscarriage, uterus eruption, and/or other adverse conditions affecting pregnancy. Several examples of common uterus variations are shown in FIG. 2 including normal 202, subseptate 204, bicornuate unicolis 206, septus 208, bicornuate 210, didelphys 212, and uncolis 214.

Diagnosis of these foregoing conditions can involve visualizing a three-dimensional image of the human anatomy along different planes. For example, as shown in FIG. 3, the human anatomy may be visualized relative to the sagittal 302, coronal 304, and transverse 306 planes of a human body. A conventional technique for visualizing the human anatomy along such planes includes manipulating the three-dimensional image of the human anatomy using rotating, panning, scaling, and/or other suitable planar editing tools that require input from the technician or doctor. Using traditional tools, this technique can be time-consuming and inefficient because it requires a significant amount of three-dimensional analysis and anatomical familiarity.

SUMMARY

An ultrasound system includes an ultrasound scanner, a link attached to the ultrasound scanner, and a processing unit operatively coupled to the ultrasound scanner via the link. The processing unit receives a first dataset representing ultrasonic scanning of a target anatomy of a patient in a two-dimensional mode. The processing unit then generates a two-dimensional ultrasound image of the scanned target anatomy based on the received first dataset and displays the generated two-dimensional ultrasound image on a display. An input defining at least one of an A-plane, a B-plane, and a C-plane with respect to the two-dimensional ultrasound image is received. Thereafter, a second dataset is received representing three-dimensional ultrasonic scanning of the target anatomy and an additional ultrasound image is generated along a plane orthogonal to the two-dimensional ultrasound image of the target anatomy based on (1) the three-dimensional ultrasonic scanning and (2) the input defining at least one of the A-plane, the B-plane, and the C-plane.

In one embodiment, the input includes placement of one or more cut lines relative to the displayed two-dimensional ultrasound image that define the desired plane. A benefit of the described invention is, for example, that it can increase the efficiency of obtaining and/or analyzing three-dimensional images, because the viewing orientation of the three-dimensional volume can be defined by the operator prior to its generation.

DETAILED DESCRIPTION

The present technology is directed to an enhanced ultrasound imaging apparatus and associated methods of work flow. As used herein, the term "three-dimensional" (or "3-D") image generally refers to an image having three dimensions that do not lie in the same plane. The term "four-dimensional" (or "4-D") image generally refers to a sequence of 3-D images over time. It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the technology. Additionally, the technology can include other embodiments that are within the scope of the claims but are not described in detail with respect to FIGS. 4A-9.

Figure 4A:
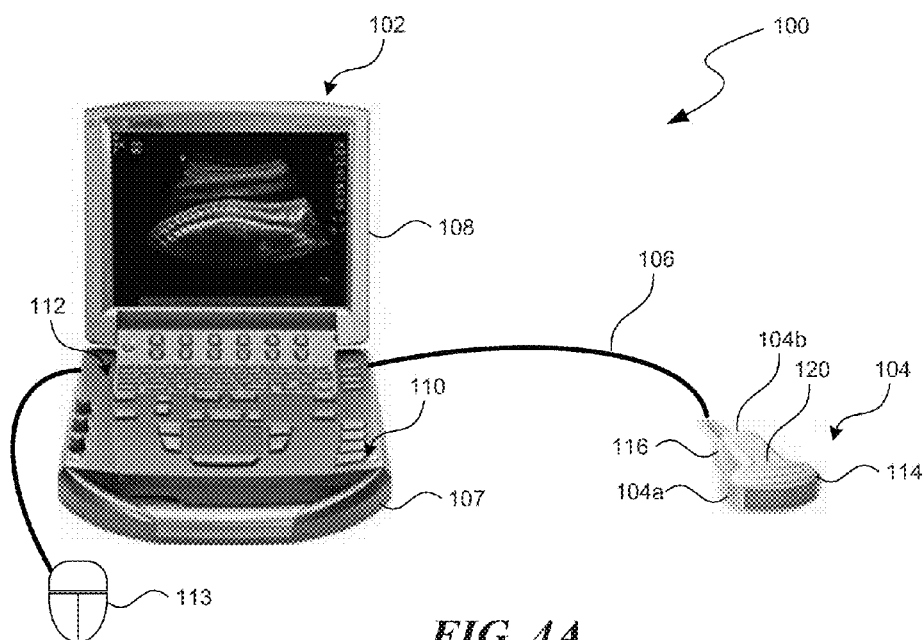
FIG. 4A is a diagram illustrating an ultrasound imaging apparatus in accordance with one embodiment.
Figure 4B:
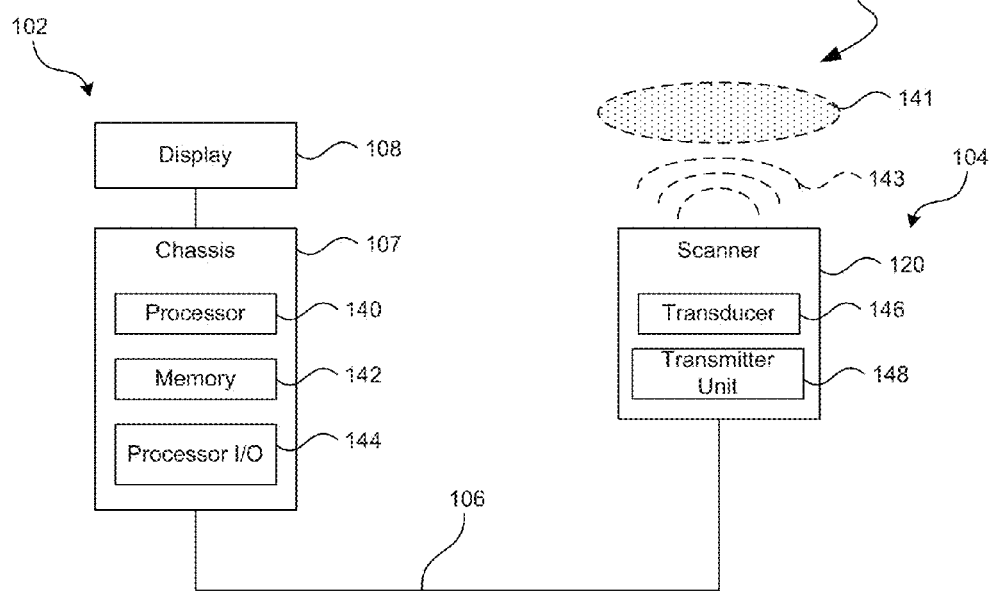
FIG. 4B is a schematic logic diagram of an ultrasound imaging apparatus.

FIG. 4A is a perspective view and FIG. 4B is a schematic logic diagram of an ultrasound imaging apparatus 100. As shown in FIG. 4A, the ultrasound imaging apparatus 100 can include a processing unit 102 coupled to an ultrasound scanner 104 with a link 106. The link 106 may provide, for example, a communication channel between the processing unit 102 and the ultra sound scanner, power distribution, sensor feedback paths, timing control and synchronization, etc. In one embodiment, the link 106 includes a plurality of coaxial or other type of hardwire cables. In other embodiments, the link 106 can include a wireless link, an internet link, an intranet link, and/or another suitable connection.

As shown in FIG. 4A, the processing unit 102 may be a cart device, a mobile device, a wall-mounted or ceiling-mounted device, or hand-held device that includes a chassis 107 operatively coupled to a display 108. The chassis 107 can include one or more buttons 110, a keyboard 112, a port for a mouse 113, a stylus (not shown), and/or other suitable input/output components. The display 108 can include a liquid crystal display, a plasma display, a touchscreen, and/or another suitable graphic display. In other embodiments, the processing unit 102 can comprises a handheld device, a cart-mounted device, a fixed-mounted device, or another suitable type of device.

The ultrasound scanner 104 can include a housing 120 with a scan head 114 at a distal end 104a and a hand grip 116 at a proximal end 104b. In the illustrated embodiment, the scan head 114 and the hand grip 116 of the ultrasound scanner 104 form generally a "T" shape. In other embodiments, the scan head 114 and the hand grip 116 can have other suitable geometric configurations based on particular applications. As described in more detail below with reference to FIG. 4B, the ultrasound scanner 104 can further include an ultrasound transducer array in the scan head 114 at the distal end 104a, electronic data processing components in the housing 120, and/or other suitable mechanical or electrical components (not shown in FIG. 4A) in the housing 120.

As shown in FIG. 4B, the processing unit 102 can include a logic processor 140, a memory 142 operatively coupled to the logic processor 140, and a processor input/output component 144. The logic processor 140 can include a microprocessor, DSP, FPGA, CPU, ASIC, a field-programmable gate array, and/or other suitable devices. The memory 142 can include volatile and/or nonvolatile computer storage media (e.g., ROM, RAM, magnetic disk storage media, optical storage media, flash memory devices, and/or other suitable non-transitory computer readable media) configured to store data received from, as well as instructions for, the logic processor 140. In operation, the processor loads and executes instructions from the memory 142 to carry out functions attributed to the processing unit 102 described below. The processor input/output component 144 can include device drivers configured to accept input from and provide output to an operator via the keyboard 112 (FIG. 4A), the buttons 110 (FIG. 4A), the display 108, a touch panel, a virtual keyboard, and/or other suitable interfacing components of the processing unit 102.

In the embodiment shown in FIG. 4B, the ultrasound scanner 104 includes an ultrasound transducer 146 operatively coupled to the processor input/output component 144 via the link 106. In one embodiment, the ultrasound transducer 146 includes a single transducer element. In other embodiments, the ultrasound transducer array 146 can include an array of individual piezoelectric transducer elements (e.g., 256 lead zirconate titanate elements) and/or other suitable transducer elements. The ultrasound scanner 104 may also include a transmitter unit 148 that provides power and transmit beamforming information to the transducer 146.

Referring to both FIGS. 4A and 4B, in operation, an operator (not shown) holds the ultrasound scanner 104 by the hand grip 116 and places the distal end 104a of the ultrasound scanner 104 proximate to or in contact with a structure to be examined, for example, a target anatomy 141 of a patient (shown in phantom lines for clarity). The transmitter unit 148 provides power and transmits beamforming information to the transducer 146. The ultrasound transducer array 146 then transmits sound waves 143 directed at the target anatomy 141 and detects echoes returning from the target anatomy 141. The ultrasound transducer array 146 can then convert the detected echoes into electrical signals representing the detected echoes.

The processing unit 102 receives the electrical signals from the ultrasound scanner 104 via the link 106 and the processor input/output component 144. The processing unit 102 can process the received electrical signals to generate, record, and/or display a two-dimensional (or "2-D") image along certain planes of the target anatomy 141 based on the received data. For example, the processing unit 102 may include logic for beamforming received signals from the ultrasound scanner (alternatively, the receive beamforming logic may be embodied in the scanner 104 itself). Furthermore, the processor 140 or other device coordinates and controls various sub-units of the processing unit 102 to carry out the functions described herein. For example, the processor 140 may load computer-executable program instructions from the memory 142 and execute the instructions to carry out these tasks. The processor 140 furthermore facilitates communications among the sub-units and manages the data flow rate and timing.

Figure 1A:
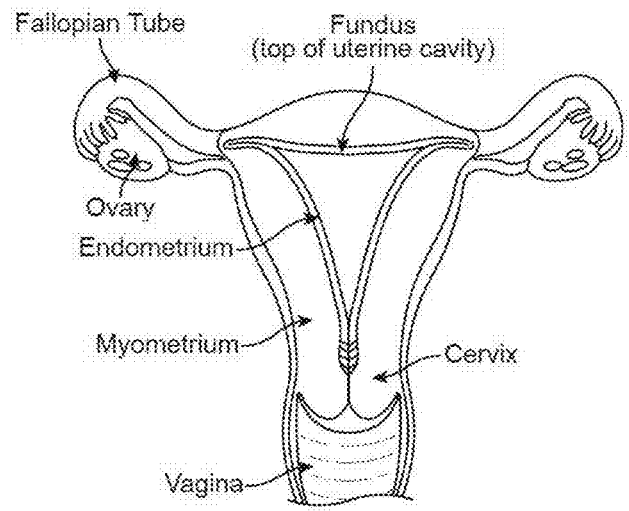
FIG. 1A is a cross-sectional view of a normal female reproductive system.
Figure 1B:
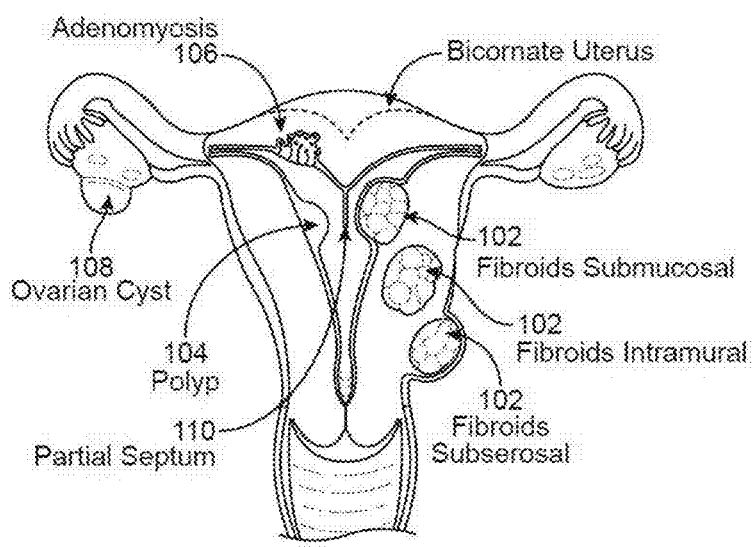
FIG. 1B is a cross-sectional view of a female reproductive system with certain abnormalities.
Figure 2:
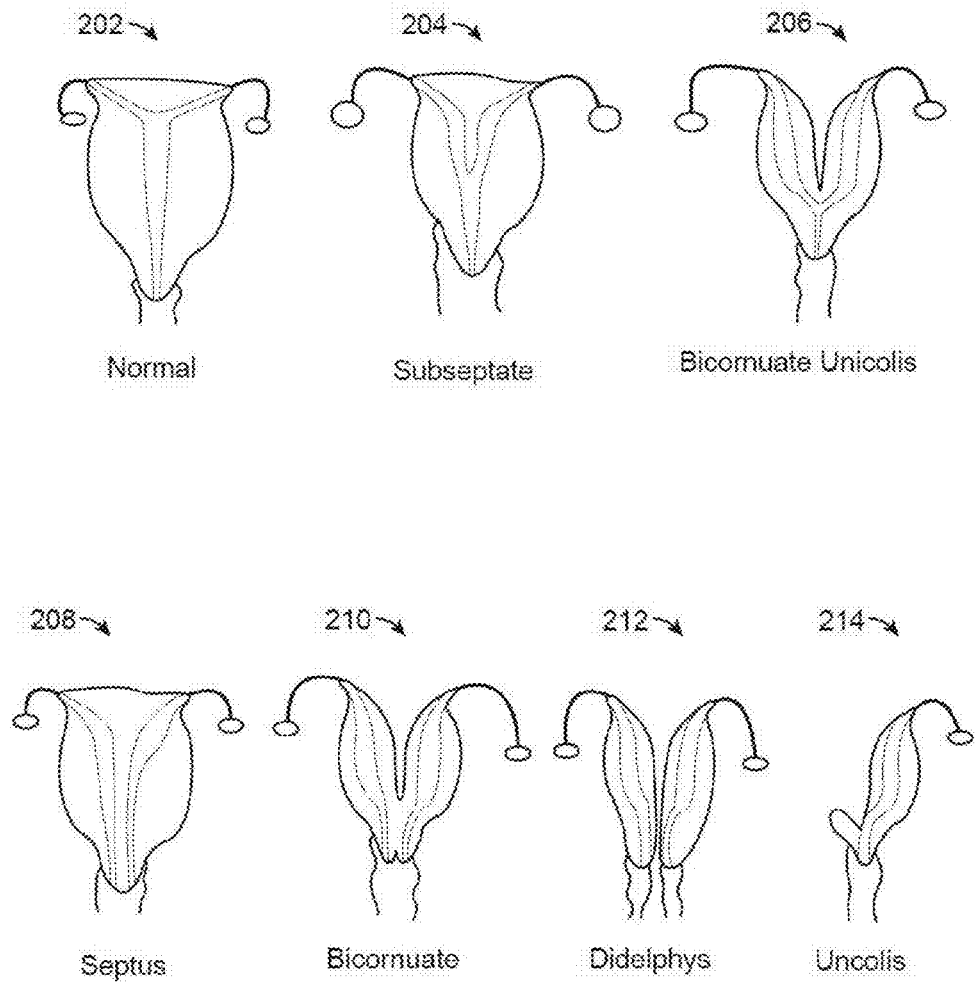
FIG. 2 illustrates certain variations in uterus shapes.
Figure 3:
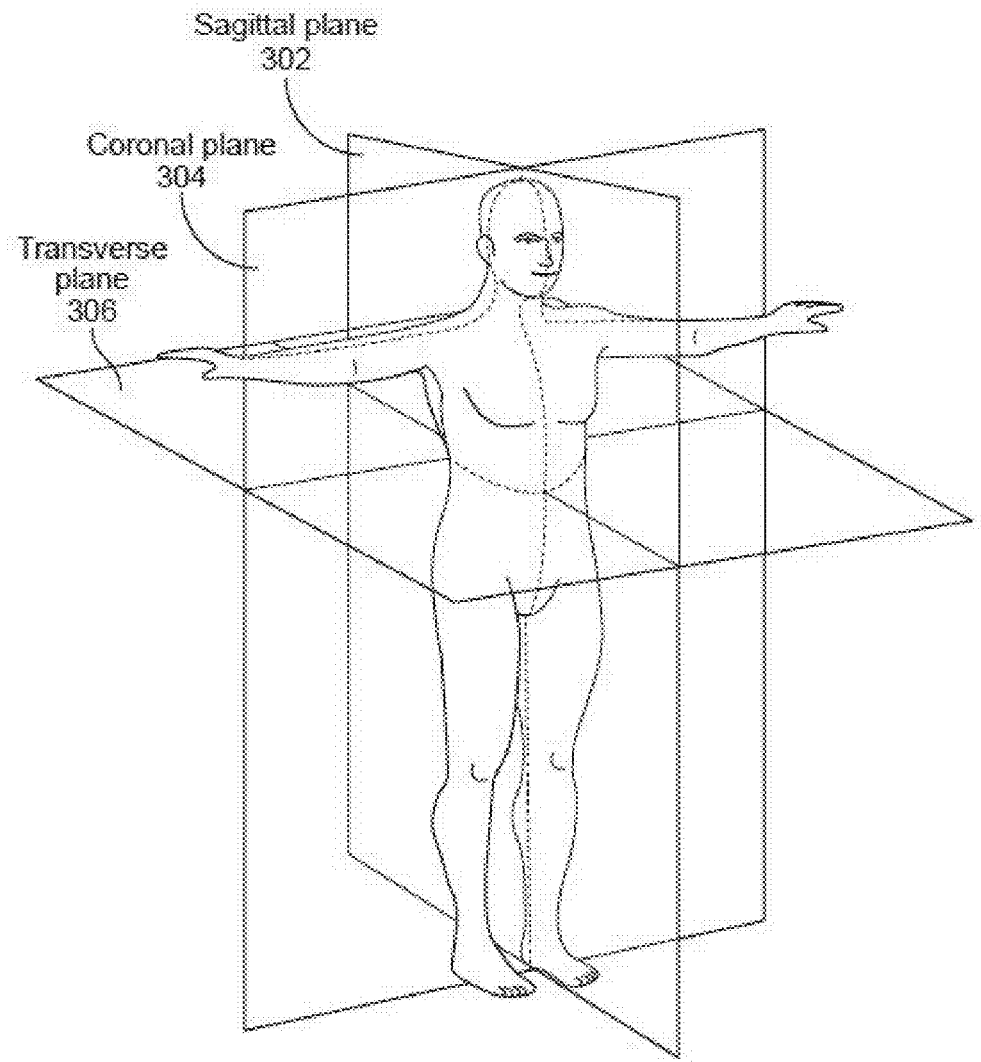
FIG. 3 is a perspective view of a human body illustrating the sagittal, coronal, and transverse planes.
Figure 5:
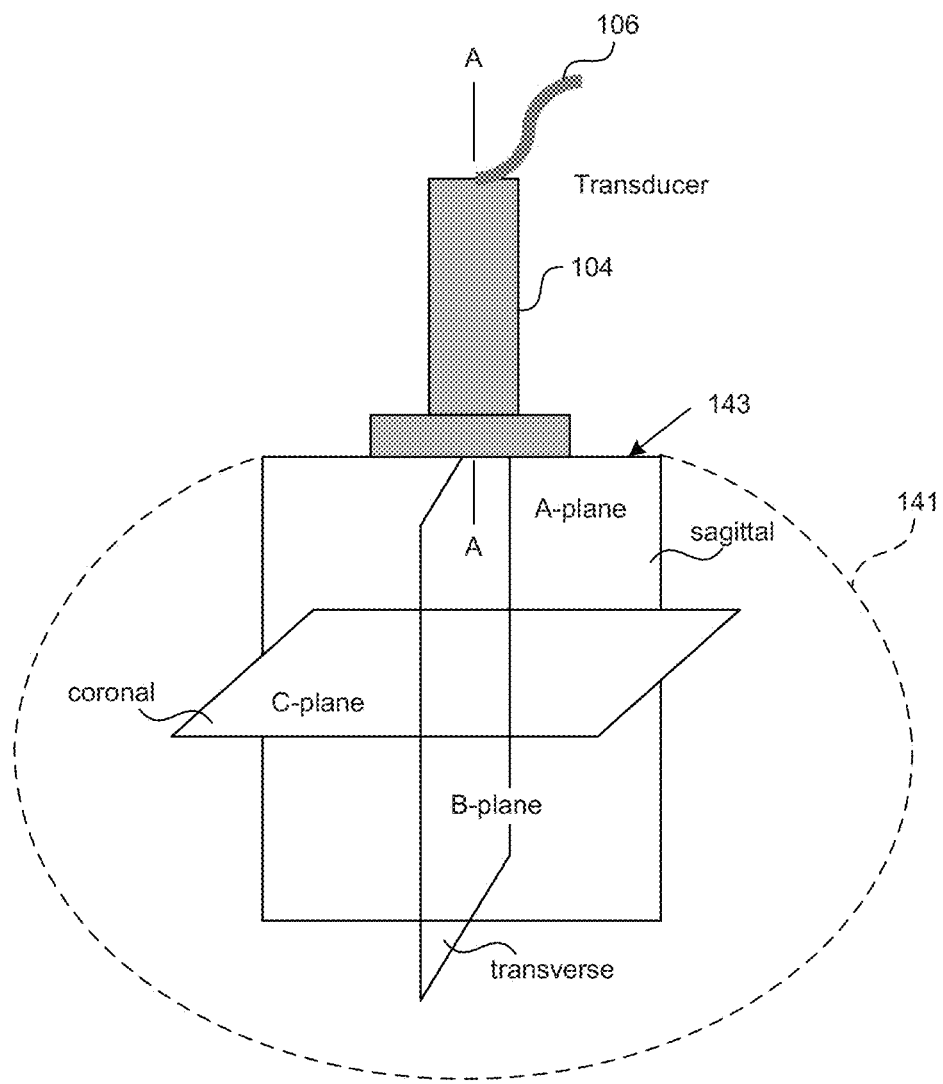
FIG. 5 is a perspective view of a target anatomy showing naming conventions for 3-D cut planes in accordance with one embodiment.

FIG. 5 is a perspective view of the target anatomy 141 showing naming conventions for 3-D cut planes or multi-planar-rendered ("MPR") planes typically available on an ultrasound display after scanning. As shown in FIG. 5, the target anatomy 141 may be divided along three generally orthogonal cut planes, i.e., an A-plane, a B-plane, and a C-plane relative to the ultrasound scanner 104. For medical diagnosis, it is often desirable to have the A-, B-, and C-planes displayed by the processing unit 102 correspond to the sagittal, transverse, and coronal planes respectively (FIG. 3) relative to a human body. However, for certain types of diagnoses, the A-, B-, and C-planes may instead be chosen to correspond to orthogonal planes oriented at different angles relative to the human body that do not necessarily correspond to the sagittal, transverse, and coronal planes as defined in FIG. 3. For example, a fetus's head may be in a position that is not necessarily lined up with the maternal body orientation that a physician relies on to position the scanner 104. As the operator rotates the ultrasound scanner 104 about axis A-A between A- and B-planes, the processing unit 102 can produce 2-D images of the target anatomy along the A-plane (e.g., the sagittal plane) and the B-plane (e.g., the transverse plane) in real-time or near real-time. However, as shown in FIG. 5, the C-plane images (e.g., the coronal plane) typically cannot be obtained by rotating the ultrasound scanner 104 because the target anatomy 141 typically blocks such a movement. In certain applications, the C-plane images are more important than the A-plane and B-plane images for diagnosing polyp, bicornuate uterus, and/or other uterus abnormalities, as shown by FIG. 2.

The C-plane images though, may be obtained through 3-D/4-D volume imaging. A conventional technique for producing C-plane images from a 3-D/4-D image involves turning and rotating the 3-D/4-D image after starting 3-D/4-D volume imaging. Such a technique, however, requires a significant amount of three-dimensional thinking and anatomical familiarity by the operator because the 3-D/4-D images typically do not include any familiar anatomic landmarks. Several embodiments of the ultrasound imaging apparatus 100 can address the foregoing drawbacks by allowing the operator to define at least one MPR plane in a 2-D image of the target anatomy 141 using familiar anatomic landmarks prior to starting 3-D/4-D volume imaging and automatically producing the C-plane images without further gross manipulation of the 3-D/4-D volume image dataset. These techniques are discussed in more detail below with reference to FIGS. 6-9.

Figure 6:
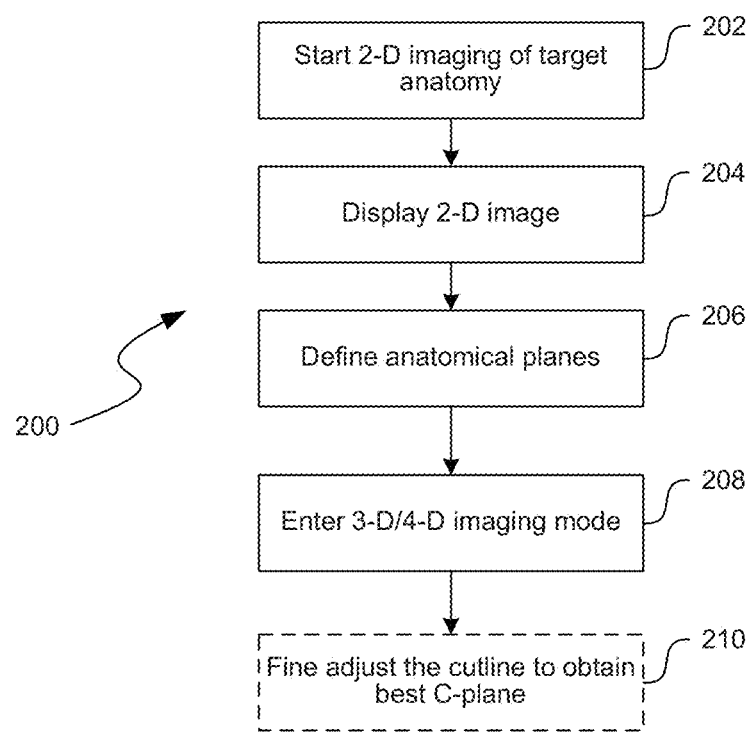
FIG. 6 is a flowchart showing a method of work flow for generating 3-D/4-D images of a target anatomy in accordance with one embodiment.

FIG. 6 is a flowchart showing a method of work flow 200 for generating cut-plane images of 3-D/4-D imaging of a target anatomy. In the following discussion, a uterus is used as an example of a target anatomy although several embodiments of the technique may also be applied to a heart, a fetus, and/or other suitable target anatomies.

As shown in FIG. 6, an initial stage of the method 200 (block 202) includes starting 2-D imaging of the uterus. In one embodiment, the processing unit 102 (FIG. 4A) can send a command to the ultrasound scanner 104 (FIG. 4A) to simultaneously scan a plane (e.g., A- or B-plane) at least proximate the target anatomy. Such scanning is typically referred to as scanning in B-mode. The processing unit 102 can then receive a first dataset that represents a 2-D image of the uterus from the ultrasound scanner 104. In another embodiment, the ultrasound scanner 104 may scan the target anatomy using line scanning (typically referred to as A-mode), and the processing unit 102 may assemble the first dataset based on the data corresponding to the A-mode scanning. In other embodiments, the processing unit 102 may receive a dataset that represents a 3-D/4-D volume scanning of the target anatomy from the ultrasound scanner 104. The processing unit 102 may then analyze the received dataset (e.g., using A-plane images) to generate the first dataset corresponding to at least one 2-D image of the uterus.

Another stage of the method 200 (block 204) can include rendering the generated 2-D image of the uterus on the display 108 (FIG. 4A). In one embodiment, the 2-D image may be generated and/or displayed when the processing unit 102 is in 2-D scanning mode. In another embodiment, the 2-D image may be displayed when the processing unit 102 is in "setup" mode before initiating 3-D/4-D scanning. In further embodiments, the 2-D image may be displayed in other suitable operating modes.

A subsequent stage of the method 200 (block 206) includes defining anatomical planes of the uterus based on the displayed 2-D image. In one embodiment, the anatomical planes can include at least one of the A-, B-, and C-planes defined by placing cut lines on the displayed 2-D image. The operator can then provide an input indicating correspondence between the cut lines and at least one of the A-, B-, and C-planes. For example, if it is desired to have the A-, B-, and C-planes correspond to sagittal, transverse, and coronal planes respectively of the human body, the operate may first obtain an A-plane image along the sagittal plane, and then, based on knowledge of the human anatomy place cut lines on the A-plane image indicating the proper orientation of the transverse and sagittal planes relative to the two-dimensional image. In another embodiment, the anatomical planes may be defined using other suitable techniques. The cut line could be straight, curved, or free-shaped to follow the anatomy. The corresponding cut plane could be a stretched out planar plane display if it is a curved plane.

Based on the defined anatomical planes, another stage (block 208) of the method 200 includes initiating 3-D/4-D volume imaging and automatically producing the A-, B-, and C-plane images. During 3-D/4-D volume imaging, the ultrasound scanner 104 may provide a second dataset to the processing unit 102 representing a volume image of the uterus. In one embodiment, the processing unit 102 may use the relative placement of the cut line(s) as a criterion and generate an additional ultrasound images that are orthogonal to the plane of the original two-dimensional ultra sound image and are oriented along the cut-lines. For example, in one embodiment, the two-dimensional ultrasound image may be an A-plane image (e.g., corresponding to a sagittal plane). The processing unit 102 may receive data (e.g., starting and/or ending coordinates of lines, shapes, etc.) representing a placement of a first cut line and a second cut line relative to the two-dimensional ultrasound image. The processing unit 102 may then receive an input indicating that the first cut line corresponds to the B-plane (e.g., a transverse plane) and that the second cut line corresponds to the C-plane (e.g., a coronal plane).

Similarly, in another embodiment, the two-dimensional ultrasound image may be a B-plane image. The processing unit 102 may receive data (e.g., starting and/or ending coordinates of lines, shapes, etc.) representing a placement of a first cut line and a second cut line relative to the two-dimensional ultrasound image. The processing unit 102 may then receive an input indicating that the first cut line corresponds to the A-plane (e.g., a sagittal plane) and that the second cut line corresponds to the C-plane (e.g., a coronal plane).

Based on the input, the processing unit 102 may then process the second dataset to generate ultrasound images at additional and/or different planes. For example, in one embodiment, the processing unit 102 generates an ultrasound image at the C-plane. In another embodiment, images along at least two of the A-plane, B-plane, and C-plane may be generated based on the operator's placement of the cut lines. An optional stage (block 210) of the method 200 includes fine-adjusting the 3-D/4-D imaging to obtain a desired C-plane image.

Figure 7A:
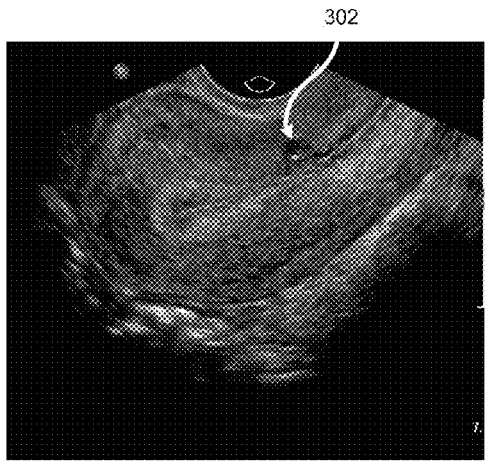
FIGS. 7A-7C are 2-D ultrasonic images of a target anatomy during certain stages of a work flow method in accordance with one embodiment.
Figure 7B:
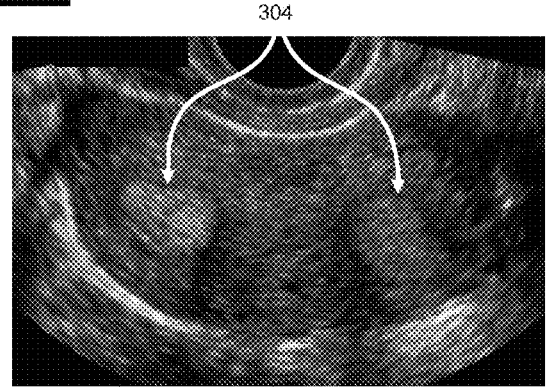
Figure 7C:
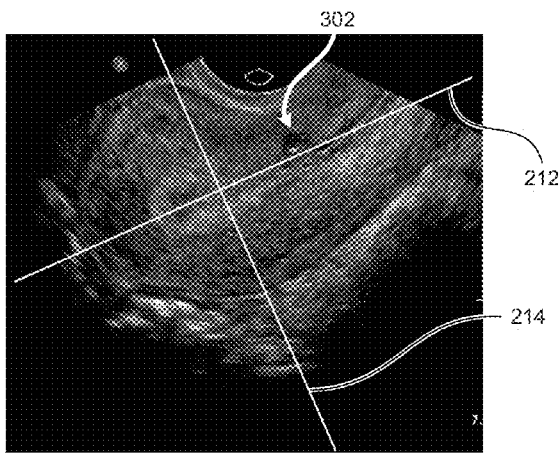

FIGS. 7A-9 illustrates ultrasonic images of the uterus during several stages of the method 200 in FIG. 6. FIGS. 7A and 7B are 2-D A-plane and B-plane views, respectively, of the uterus. In FIG. 7A, the illustrated image shows a scar 302 from a previous Caesarian section. In FIG. 7B, the illustrated image shows a bicornuate uterus 304. An operator can then define anatomical planes of the target anatomy based on the displayed 2-D image. For example, as shown in FIG. 7C, the operator may define the B-plane and the C-plane by placing the first and second cut lines 212 and 214 on the displayed 2-D image, respectively. The first and second cut lines 212 and 214 may be placed by defining a starting point and an end point of the first and second cut lines 212 and 214, by drawing a line with the mouse 113 (FIG. 4A), or by drawing a line with a finger on a touch panel, and/or via other suitable means.

Figure 8:
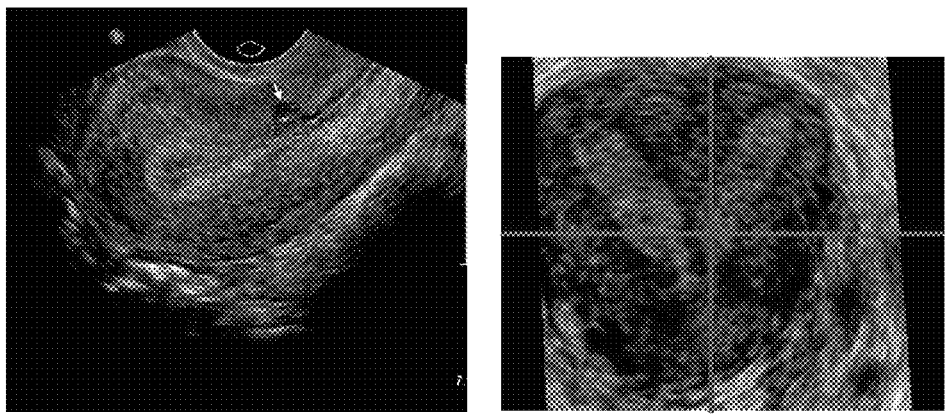
FIGS. 8 and 9 are ultrasonic images of a target anatomy during other stages of a work flow method in accordance with one embodiment.
Figure 9:
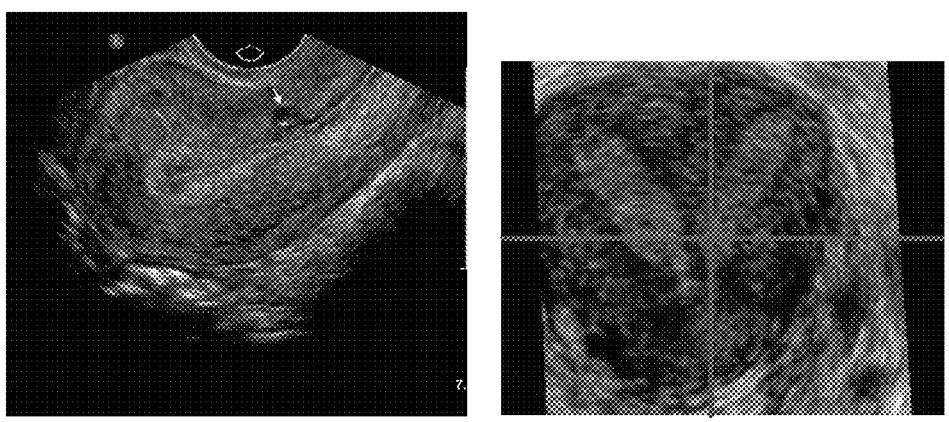
Figure 9:
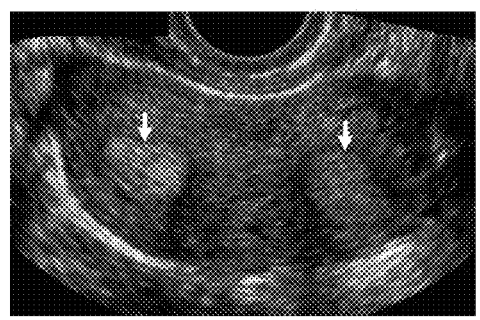

Subsequently, 3-D/4-D volume imaging may be started. Based on the cut lines defined in FIG. 7C, images at different anatomical planes may be automatically generated. For example, FIG. 8 shows the images at the A-plane and the C-plane in a side-by-side arrangement. In another example, as shown in FIG. 9, the images at the A-plane (upper left), the B-plane (lower), and the C-plane (upper right) may be shown together. In further examples, at least some of these images may be shown with the 3-D/4-D images, and/or may have other suitable display configurations.

From the foregoing, it will be appreciated that specific embodiments of the technology have been described herein for purposes of illustration, but that various modifications may be made without deviating from the disclosure. Many of the elements of one embodiment may be combined with other embodiments in addition to or in lieu of the elements of the other embodiments. Accordingly, the disclosure is not limited except as by the appended claims.

The invention claimed is:

1. A method of operating an ultrasound imager to perform ultrasound scanning, comprising:
receiving a first dataset representing an ultrasonic scanning of a target anatomy of a patient in a two-dimensional mode in one of a sagittal, transverse or coronal anatomical plane;
generating a first two-dimensional ultrasound image of the scanned target anatomy based on the received first dataset;
displaying the first two-dimensional ultrasound image of the scanned target anatomy;
receiving an input defining at least an orientation of a first cut line and a second cut line on the displayed first two-dimensional ultrasound image and a correspondence between the first and second cut lines and the other of the sagittal, transverse or coronal anatomical planes that are orthogonal to the plane of the first two-dimensional ultrasound image; and
thereafter, receiving a second dataset representing three-dimensional ultrasonic scanning of the target anatomy and generating and displaying ultrasound images in at least two of the sagittal, transverse and coronal anatomical planes based on (1) the three-dimensional ultrasonic scanning dataset and (2) the orientation of the first and second cut lines and their correspondence to the sagittal, transverse or coronal anatomical planes that are orthogonal to the plane of the first two-dimensional ultrasound image.

2. The method of claim 1,
wherein the displayed first two-dimensional ultrasound image represents the sagittal anatomical plane; and
wherein receiving the input includes:
receiving placement of the first out line relative to the displayed first two-dimensional ultrasound image; and
receiving an input indicating that the first cut line corresponds to one of the transverse or coronal anatomical planes.

3. The method of claim 1,
wherein the displayed first two-dimensional ultrasound image represents the transverse anatomical plane; and
wherein receiving the input includes:
receiving placement of the first cut line relative to the displayed two-dimensional ultrasound image; and
receiving an input indicating that the first cut line corresponds to one of the sagittal or coronal anatomical planes.

4. The method of claim 1,
wherein the displayed first two-dimensional ultrasound image represents the sagittal anatomical plane; and
wherein receiving the input includes:
receiving placement of the first cut line and the second cut line relative to the displayed first two-dimensional ultrasound image; and
receiving an input indicating that the first cut line corresponds to the transverse anatomical plane and the second cut line corresponds to the coronal anatomical plane.

5. The method of claim 1,
wherein the displayed first two-dimensional ultrasound image represents the transverse anatomical plane; and
wherein receiving the input includes:
receiving placement of the first cut line and the second cut line relative to the displayed first two-dimensional ultrasound image; and
receiving an input indicating that the first cut line corresponds to the sagittal anatomical plane and the second cut line corresponds to the coronal anatomical plane.

6. The method of claim , wherein receiving the first dataset comprises:
receiving signals acquired by a transducer via a beamformed transmit waveform.

7. The method of claim 1, wherein generating the two-dimensional ultrasound image comprises:
applying beamforming to the first dataset to generate a beamformed representation;
processing the beamformed representation to form time-varying 2D or 3D images.

8. An ultrasound system, comprising:
an ultrasound scanner;
a link attached to the ultrasound scanner; and
a processing unit operatively coupled to the ultrasound scanner via the link, the processing unit having a display, a processor, and a non-transitory computer-readable medium containing instructions that, when executed, cause the processor to perform a method comprising:
receiving a first dataset from the ultrasound scanner, the first dataset representing ultrasonic scanning of a target anatomy of a patient in a two-dimensional mode in one of a sagittal, transverse or corona anatomical planes;
generating a first two-dimensional ultrasound image of the scanned target anatomy based on the received first dataset;
displaying the generated first two-dimensional ultrasound image on the display;
receiving an input defining at least an orientation of a first cut line and a second cut line on the displayed first two-dimensional ultrasound image and a correspondence between the first and second cut lines and the others of the sagittal, transverse and coronal anatomical planes that are orthogonal to the plane of the displayed first two-dimensional ultrasound image; and
thereafter receiving a second dataset representing ultrasonic scanning of the target anatomy in a three-dimensional mode from the ultrasound scanner and generating an additional ultrasound image that is orthogonal to the anatomical plane of the first displayed ultrasound image based on (1) the three-dimensional scanning and (2) the orientation of the first and second cutline and their correspondence to the sagittal, transverse or coronal anatomical planes that are orthogonal to the anatomical plane of the first displayed ultrasound image.

9. The ultrasound system of claim 8,
wherein the displayed first two-dimensional ultrasound image represents the sagittal anatomical; and
wherein receiving the input includes:
receiving placement of the first cut line relative to the displayed first two-dimensional ultrasound image; and
receiving an input indicating that the first cut line corresponds to one of the transverse and coronal anatomical planes.

10. The ultrasound system of claim 8,
wherein the displayed first two-dimensional ultrasound image represents the transverse anatomical plane; and
wherein receiving the input includes:

receiving placement of the first cut line relative to the displayed first two-dimensional ultrasound image; and receiving an input indicating that the first cut line corresponds to one of the transverse and coronal anatomical planes.

\* \* \* \* \*